United States Patent [19]

Hesselgren

[11] 3,932,607

[45] Jan. 13, 1976

[54] ANTIMICROBIAL COMPOSITION

[76] Inventor: Sven-Gunnar Hesselgren, Angsholmen, Drottningholm, Sweden

[22] Filed: July 26, 1973

[21] Appl. No.: 382,815

[30] Foreign Application Priority Data
July 31, 1972 Sweden............................. 9953/72

[52] U.S. Cl. .................... 424/52; 252/106; 424/49; 424/54; 424/319
[51] Int. Cl.² ..................... A61K 7/16; A61K 27/00
[58] Field of Search ................ 424/319, 49, 54, 52

[56] References Cited
FOREIGN PATENTS OR APPLICATIONS
1,098,416    4/1965    United Kingdom OTHER PUBLICATIONS
Bandeally et al., Chem. Abst., Vol. 63 (1965), p. 13961h.

Primary Examiner—Frederick E. Waddell

[57] ABSTRACT

An antimicrobial composition comprising as active ingredients dodecyl-di-(aminoethyl)-glycine and chlorohexidine or salts thereof.

11 Claims, No Drawings

ANTIMICROBIAL COMPOSITION

The present invention relates to a new antimicrobial composition which can be used with advantage, for example, in the practice of odontology.

Dodecyl-di-(aminoethyl)-glycine (hereinafter referred to as DAG), is referred to as amphoteric electrolytes, normally known as ampholyte soap. These substances, which are thus both anionic and cationic, combine the bactericidal properties of the cationic substances with the surface active and soil dissolving properties of the anionic substances. Contrary thereto, for example, to the invert soaps, the ampholyte soaps together with protein result only in negligible precipitations or none at all. It is known that in weak concentrations and over short periods of exposure DAG is effective against gram positive and gram negative bacteria as well as against fungus. There is, however, no record of the effect of the compound on oral microflora and the possibility of using it in the practice of odontology.

It is also known that chlorohexidine is effective against gram positive and gram negative bacteria as well as against fungus. Chlorohexidine, which is a base, can be used in the form of salts, such as digluconate (easily soluble in water), diacetate (less soluble in water than digluconate), dichloride (soluble in water to only 0.06 %) or monofluorophosphate.

Surprisingly, it has now been found according to the present invention, that DAG in combination with chlorohexidine or salts thereof produces an antimicrobial composition or inhibitor which has a synergistic effect on the organisms and materials mentioned above.

The antimicrobial composition according to the present invention is conveniently characterised in that it contains as the active components dodecyldi-(aminoethyl)-glycine and chlorohexidine or salts of these.

The invention is not limited to any specific proportions of the two components since it has been found that even slight amounts of one of the components in proportion to the quantity of the other components with corresponding quantities of active substance produces a synergistic effect in comparison to the effects of the individual components. The proportions and the total quantity of active substance are selected with respect to the mutual toxicity of the two components, the intended application, effect and form of application.

The following are details relative to a number of tests performed by using DAG and chlorohexidine digluconate, 1,1'-hexamethylene bis-[5-(p-chlorophenyl)-biguanide]-digluconate, separately and with compositions according to this invention, i.e. containing DAG and chlorohexidine digluconate. Equal parts (by weight) of the two components were used in the combined compositions unless otherwise stated.

In the tests pure cultivated cultures of the microorganisms Streptococcus faecalis and Escherichia coli were used as well as homogenized dental plaque material in various environments such as phosphate buffer and sterile saliva. The technical method for cultivation, isolation, collecting and preparing the homogeneous suspensions of the microorganisms was performed in the conventional manner. Dental plaque was taken from one person in direct connection with performing the tests, the plaque being collected in the morning before any precautions towards oral hygiene had been taken. Fresh saliva was collected from a number of donors and radiation-sterilized with Cobalt 60 (Radona Irradiation, Skarhamn, Sweden) in sealed glass tubes, the radiation dose being 3.2 M rad.

The tests were carried out at 37° C after preparatory inhibition tests at 20° and 37° C showed no difference in the degree of inactivation.

Water solutions with various concentrations of the three different types of inhibitors were prepared from a basic solution of dodecyldi-(aminoethyl)-glycine (TH. Goldschmidt, A.G., Chemische Fabriken, Essen, West-Germany) and from chlorohexidine digluconate (ICI, Great Britain).

The tests were carried out in the following manner:

1 ml of the homogenized bacteria suspensions or the homogenized test material was mixed with 1 ml inhibitor solution in 8 ml sterile phosphate buffer or 8 ml sterilized saliva. After expiration of the exposure time a suitable amount of the mixture was membrane filtered and washed with sterile water to remove the inhibitor from the filter (Millipore, MF. HA 0.45 millimikron). In order to calculate the number of reproducible cells, incubation was carried out at 37° C for 24 – 48 hours with the membrane filter placed on blood agar plates (5 % horse blood). The number of washes required to eliminate the inhibitor was determined by separate experiments with the strongest concentration of the inhibitors used and with a bacteria suspension of known density.

The results of the tests carried out are given in the following tables which show the number of surviving organisms expressed in logarithmic numbers after 4 minutes inhibitor exposure. A indicates dodecyl-di-(aminoethyl)-glycine (DAG), B chlorohexidine digluconate and C the combination of these two substances. "Control" means no inhibitor in the solutions.

Table 1 shows the results of tests using washed bacteria suspensions of *Escherichia coli* in phosphate buffer having a pH value of 7.0.

TABLE 1

| Inhibitor | Amount of active substance, mg/ml | | | | Control |
|---|---|---|---|---|---|
| | 0.001 | 0.01 | 0.1 | 1.0 | |
| A | $2 \cdot 10^6$ | $2 \cdot 10^6$ | $1 \cdot 10^2$ | 0 | $2 \cdot 10^6$ |
| B | $2 \cdot 10^4$ | $2 \cdot 10^2$ | 0 | 0 | $2 \cdot 10^6$ |
| C | $6 \cdot 10^5$ | $2 \cdot 10^0$ | 0 | 0 | $2 \cdot 10^6$ |

From the above it is clear that 0.001 and 0.01 mg/ml of inhibitor A (DAG) did not affect the original number of bacteria in the suspentions ($2.10^6$). With inhibitor B (chlorohexidine salt) in corresponding concentrations a reduction of bacteria was obtained which, shown graphically, indicates an exponential course. With inhibitor mixture C (DAG + chlorohexidine salt) only slight inactivation was shown with the 0.001 mg/m concentration, but the bactericidal effect at 0.01 mg/ml and stronger concentrations was greater than that obtained when using DAG or chlorohexidine alone.

Table 2 shows the results of corresponding test with bacteria suspensions of *Streptococcus faecalis*.

TABLE 2

| Inhibitor | Amount of active substance, mg/ml | | | | Control |
|---|---|---|---|---|---|
| | 0.001 | 0.01 | 0.1 | 1.0 | |
| A | $2 \cdot 10^6$ | $2 \cdot 10^6$ | $3 \cdot 10^2$ | 0 | $2 \cdot 10^6$ |
| B | $1 \cdot 10^5$ | $5 \cdot 10^2$ | $7 \cdot 10^0$ | 0 | $2 \cdot 10^6$ |
| C | $2 \cdot 10^6$ | $8 \cdot 10^1$ | 0 | 0 | $2 \cdot 10^6$ |

In these corresponding tests with *Streptococcus faecalis*, as is clear from Table 2, differences in inactivation ability were found to be similar to those obtained in the tests according to Table 1.

In agreement with this example, comparative tests were carried out with the various inhibitors on bacteria suspensions of *Streptococcus faecalis* in sterile saliva having a pH value of 7.3. The results are shown in Table 3.

TABLE 3

| Inhibitor | Amount of active substance, mg/ml | | | | Control |
|---|---|---|---|---|---|
| | 0.001 | 0.01 | 0.1 | 1.0 | |
| A | $1 \cdot 10^7$ | $1 \cdot 10^7$ | $1 \cdot 10^7$ | $1 \cdot 10^4$ | $1 \cdot 10^7$ |
| B | $1 \cdot 10^7$ | $7 \cdot 10^6$ | $5 \cdot 10^3$ | $9 \cdot 10^2$ | $1 \cdot 10^7$ |
| C | $1 \cdot 10^7$ | $5 \cdot 10^6$ | $7 \cdot 10^2$ | $1 \cdot 10^0$ | $1 \cdot 10^7$ |

The results show that higher concentrations of the inhibitors were required in saliva in order to achieve the same level of bacteria reduction as in the phosphate buffer. The relationship between the effect of the various inhibitors was, however, the same as in the preceding tests.

Additional tests were carried out to investigate the effect of the various inhibitors on homogenized dental plaque in phosphate buffer with a pH value of 7.0. The plaque material was subjected to aerobic cultivation and anaerobic cultivation. The results obtained are shown in Table 4 (aerobic cultivation) and table 5 (anaerobic cultivation).

TABLE 4

| Inhibitor | Amount of active substance, mg/ml | | | | Control |
|---|---|---|---|---|---|
| | 0.001 | 0.01 | 0.1 | 1.0 | |
| A | $1 \cdot 10^7$ | $7 \cdot 10^6$ | $1 \cdot 10^6$ | $3 \cdot 10^2$ | $1 \cdot 10^7$ |
| B | $1 \cdot 10^7$ | $1 \cdot 10^6$ | $5 \cdot 10^4$ | $7 \cdot 10^2$ | $1 \cdot 10^7$ |
| C | $1 \cdot 10^7$ | $1 \cdot 10^5$ | $1 \cdot 10^3$ | $1 \cdot 10^1$ | $1 \cdot 10^7$ |

TABLE 5

| Inhibitor | Amount of active substance, mg/ml | | | | Control |
|---|---|---|---|---|---|
| | 0.001 | 0.01 | 0.1 | 1.0 | |
| A | $7 \cdot 10^7$ | $9 \cdot 10^6$ | $2 \cdot 10^6$ | $2 \cdot 10^2$ | $7 \cdot 10^7$ |
| B | $7 \cdot 10^7$ | $7 \cdot 10^6$ | $8 \cdot 10^4$ | $3 \cdot 10^3$ | $7 \cdot 10^7$ |
| C | $7 \cdot 10^7$ | $7 \cdot 10^5$ | $6 \cdot 10^4$ | $1 \cdot 10^0$ | $7 \cdot 10^7$ |

From the above values it is clear that the mutual relationship between the inactivation ability of the various preparations on plaque was the same as in the previously recorded tests using pure cultures. Thus, inhibitor A (DAG) gave the lowest effect and inhibitor C, i.e. the combination of DAG and chlorohexidine salt the highest effect with comparable concentrations of the inhibitors.

Corresponding tests using homogenized dental plaque suspended in saliva showed that higher concentrations of the inhibitors were needed to achieve corresponding results to those obtained with phosphate buffer. However, the mutual relationship between the antimicrobial ability of the three preparations remained unchanged.

The increased degree of inactivation caused by the combination composition (C) in comparison with DAG (A) and chlorohexidine (B) in corresponding concentrations is attributed to a synergistic effect of the components being present in the combination.

In order to investigate whether NaF had any influence on the effect of the inhibitors when used on pure cultivated bacteria or mixed microflora in dental plaque material, supplementary tests were carried out with additions of sodium fluoride (NaF) to the combination inhibitor consisting of DAG mixed with chlorohexidine digluconate. Separate experiments have shown that NaF in itself does not have any bactericidal properties or effects on the microorganisms examined.

Table 6 thus shows the results obtained from tests carried out with the combination inhibitor C, i.e. containing equal parts by weight of DAG and chlorohexidine digluconate. An addition of 30 g NaF per ml inhibitor solution was used in the second part of the experiment, which was performed in an aqueous milieu, as well as in the third part of the experiment, which was performed in a saliva milieu. The test organism used was *Streptococcus faecalis*. As before, Table 6 indicates the number of surviving organisms after 4 minutes exposure to the inhibitor.

TABLE 6

| Inhibitor | Amount of active substance, mg/ml | | | | Control |
|---|---|---|---|---|---|
| | 0.001 | 0.01 | 0.1 | 1.0 | |
| C | $2 \cdot 10^7$ | $8 \cdot 10^2$ | 0 | 0 | $2 \cdot 10^7$ |
| C + NaF in aqueous milieu | $2 \cdot 10^7$ | $3 \cdot 10^3$ | 0 | 0 | $2 \cdot 10^7$ |
| C + NaF in saliva milieu | $2 \cdot 10^7$ | $2 \cdot 10^7$ | $5 \cdot 10^6$ | 0 | $2 \cdot 10^7$ |

Two more tests were carried out with inhibitor solutions containing fluoride. These solutions are designated D and contained per unit volume 10 mg DAG, 1 mg chlorohexidine digluconate and 30 mg NaF. In one test the test organism was *Streptococcus faecalis* whereas in the other test dental plaque was used as test material.

The results of these two tests are shown in Tables 7 and 8 in the order mentioned, the tables indicating the number of living organisms remaining after 4 minutes exposure to the inhibitor.

TABLE 7

| Inhibitor | Amount of active substance, mg/ml | | Control |
|---|---|---|---|
| | 0.001 | 0.01 | |
| D | $3 \cdot 10^5$ | 0 | $5 \cdot 10^6$ |

TABLE 8

| Inhibitor | Amount of active substance, mg/ml | | | Control |
|---|---|---|---|---|
| | 0.001 | 0.01 | 0.1 | |
| D | $4 \cdot 10^6$ | $6 \cdot 10^3$ | 0 | $5 \cdot 10^6$ |

It is clear from the results of these three series of tests (Tables 6 to 8) in comparison to previous tests, that 30 mg NaF per ml inhibitor solution did not affect the degree of inactivation of the inhibitors according to the present invention, but the same result was obtained as in the tests carried out without the addition of NaF. This was true both for pure cultivated bacteria and for dental plaque material which was suspended either in a phosphate buffer or in saliva.

In additional tests the bactericidal effect of the combination preparation of *Streptococcus faecalis* was investigated using varying proportions of the two combined components and at the same time a comparison was made with the individual inhibitors. Four inhibitor solutions E, F. G. H were tested with different concentrations of active substance. In relative numbers and in the order mentioned, these solutions contained 1.0 part DAG (E), 0.1 part chlorohexidine digluconate + 0.9 parts DAG (F), 1.0 part chlorohexidine digluconate (G), and 0.9 parts chlorohexidine digluconate + 0.1 part DAG (H).

The number of living organisms remaining after 4 minutes exposure to the inhibitors is stated in the following Table 9.

TABLE 9

| Inhibitor | Amount of active substance, mg/ml | | | Control |
|---|---|---|---|---|
| | 0.001 | 0.01 | 0.1 | |
| E | $1 \cdot 10^7$ | $1 \cdot 10^7$ | $3 \cdot 10^4$ | $1 \cdot 10^7$ |
| F (comb) | $7 \cdot 10^6$ | $2 \cdot 10^6$ | $8 \cdot 10^3$ | $1 \cdot 10^7$ |
| G | $5 \cdot 10^6$ | $5 \cdot 10^5$ | $7 \cdot 10^1$ | $1 \cdot 10^7$ |
| H (comb) | $2 \cdot 10^6$ | $3 \cdot 10^5$ | $2 \cdot 10^1$ | $1 \cdot 10^7$ |

It is clear from the above results that there was a synergistic effect with both the combination preparations F and H. Thus, a slight addition of chlorohexidine digluconate to a larger amount of DAG (inhibitor F) gave an increased bactericidal effect in comparison with a corresponding active substance amount of DAG (inhibitor E) at all the concentrations used and conversely, a slight addition of DAG to a larger amount of chlorohexidine digluconate (inhibitor H) gave an increased bactericidal effect in comparison with chlorhexidine digluconate (inhibitor G) in corresponding amounts of active substance.

On the basis of the tests carried out which show the anti-microbial effect of chlorohexidine digluconate and DAG at various concentrations and the synergistic effect upon combining these two substances, as well as that additions of NaF do not affect the inactivation ability of the combination preparation, the following example is given as a solution suitable for use on tooth tissue in order to achieve an optimal antimicrobial effect in combination with a maximum of fluorine protection so as to prevent or reduce the occurrence of caries. The combination preparation is extremely surface active and soil dissolving, which is of considerable importance, for example when washing out tooth cavities or treating contaminated objects. Histological investigations as to the effect the combination preparation has on the dentine and the tooth pulp show that the preparation does not produce any apparent damages to healthy tissue when applied locally.

| Example | |
|---|---|
| Chlorohexidine digluconate | 0.1 g |
| Dodecyl-di-(aminoethyl)-glycine | 1.0 g |
| NaF | 3.0 g |
| $H_2O$, ad. | 100 ml |

This antiseptic solution has a pH value of 7.3, around which value its maximum bactericidal effect also exists.

The microbicidal composition according to the present invention may be used in a multitude of different applications and forms. Apart from the above solution, it may be in the form of another antiseptic as for example in sucking or chewing tablets or a salve with or without the addition of a suitable fluorine compound.

The composition may also be included in other types of oral or dentifrice preparations, such as toothpastes and tooth creams, or be mixed with conventional agents such as abrasives, polishing agents, detergents, foam-forming agents, flavors, fluorine compounds, etc., to provide such dentifrices. The composition may be used as such or with suitable additives as an agent for disinfecting surgical areas, tooth root channels, surgical instruments, odontological material, dental technical pieces of work and the like.

The fluorine compounds mentioned above in various contexts, which are used to prevent caries, may consist of any suitable compound containing fluorine which is conventionally used in oral preparations or dentifrices and which has a beneficial effect on the care and hygiene of the oral cavity, for example for reducing the solubility of the tooth enamel in acid and protecting the teeth against caries. In addition to the sodium fluoride mentioned above, potassium fluoride, stannous fluoride, sodium stannous fluoride, sodium monofluorophosphate, etc., may be used for this purpose.

The invention is not limited to the use of chlorohexidine or chlorohexidine digluconate and DAG in the combination, but any other suitable salts of chlorohexidine and any suitable salts of DAG having a microbicidal effect can be utulized.

What I claim is:

1. An oral antibacterial composition of a pH of 7 to about 7.3 comprising as an essential active ingredient an antibacterially effective combination of (a) dodecyl-di-(aminoethyl)-glycine and (b) chlorohexidine or a salt thereof selected from the group consisting of the digluconate, the diacetate, the dichloride and the monofluorophosphate, in a suitable carrier.

2. Antibacterial composition according to claim 1, wherein the composition also contains a fluorine compound which has a beneficial effect on the care and hygiene of the oral cavity.

3. Antimicrobial composition according to claim 2, wherein the composition is in the form of a water solution containing about 0.1 g chlorohexidine digluconate, about 1.0 g dodecyl-di-(aminoethyl)-glycine and about 3.0 g sodium fluoride.

4. An antibacterial composition according to claim 3 having a pH of about 7.3.

5. An antibacterial composition according to claim 1 containing about 0.9 parts (a) to about 0.1 parts (b).

6. An antibacterial composition according to claim 1 containing about 0.1 parts (a) to about 0.9 parts (b).

7. A method of treating the oral cavity comprising applying thereto an antibacterial effective amount of the composition as defined in claim 1.

8. The composition according to claim 1 wherein the carrier is a dentifrice.

9. The composition as defined in claim 8 additionally comprising a detergent material and an effective amount of a compatible flavor.

10. The composition of claim 1 in the form of a chewable detal tablet.

11. The composition of claim 1 in the form of a mouthrinse.

* * * * *